United States Patent
Pan et al.

(10) Patent No.: US 11,459,279 B2
(45) Date of Patent: *Oct. 4, 2022

(54) SUPPORTED CATALYST AND METHOD FOR PREPARING LIGHT OLEFIN USING DIRECT CONVERSION OF SYNGAS

(71) Applicant: DALIAN INSTITUTE OF CHEMICAL PHYSICS, CHINESE ACADEMY OF SCIENCES, Dalian (CN)

(72) Inventors: Xiulian Pan, Dalian (CN); Feng Jiao, Dalian (CN); Xinhe Bao, Dalian (CN); Gen Li, Dalian (CN)

(73) Assignee: DALIAN INSTITUTE OF CHEMICAL PHYSICS, CAS, Dalian (CN)

( * ) Notice: Subject to any disclaimer, the term of this patent is extended or adjusted under 35 U.S.C. 154(b) by 58 days.

This patent is subject to a terminal disclaimer.

(21) Appl. No.: 16/963,172

(22) PCT Filed: Jan. 28, 2019

(86) PCT No.: PCT/CN2019/073386
§ 371 (c)(1),
(2) Date: Jul. 17, 2020

(87) PCT Pub. No.: WO2019/144952
PCT Pub. Date: Aug. 1, 2019

(65) Prior Publication Data
US 2021/0347710 A1   Nov. 11, 2021

(30) Foreign Application Priority Data
Jan. 26, 2018   (CN) ............ 20180079249.4

(51) Int. Cl.
C07C 1/04 (2006.01)
B01J 21/04 (2006.01)
B01J 21/06 (2006.01)
B01J 21/08 (2006.01)
B01J 21/10 (2006.01)
B01J 23/06 (2006.01)
B01J 23/08 (2006.01)
B01J 23/10 (2006.01)
(Continued)

(52) U.S. Cl.
CPC ............ C07C 1/044 (2013.01); B01J 21/04 (2013.01); B01J 21/063 (2013.01); B01J 21/066 (2013.01); B01J 21/08 (2013.01); B01J 21/10 (2013.01); B01J 23/06 (2013.01); B01J 23/08 (2013.01); B01J 23/10 (2013.01); B01J 23/18 (2013.01); B01J 23/26 (2013.01); B01J 23/34 (2013.01); B01J 29/78 (2013.01); B01J 29/783 (2013.01); B01J 35/0006 (2013.01); B01J 35/1014 (2013.01); B01J 35/1019 (2013.01); B01J 37/04 (2013.01);

*C07C 2521/04* (2013.01); *C07C 2521/06* (2013.01); *C07C 2521/08* (2013.01); *C07C 2521/10* (2013.01); *C07C 2523/06* (2013.01); *C07C 2523/08* (2013.01); *C07C 2523/10* (2013.01); *C07C 2523/18* (2013.01); *C07C 2523/24* (2013.01); *C07C 2523/34* (2013.01); *C07C 2529/76* (2013.01)

(58) Field of Classification Search
CPC ... B01J 23/06; B01J 23/08; B01J 23/10; B01J 23/18; B01J 23/26; B01J 23/34; B01J 23/745; B01J 23/75; B01J 29/185; B01J 29/14; B01J 29/24; B01J 29/26; B01J 2523/08; B01J 2523/10; B01J 2523/18; B01J 2523/26; C07C 2529/26
See application file for complete search history.

(56) References Cited

U.S. PATENT DOCUMENTS

2005/0013773 A1   1/2005   Cornelius et al.
2017/0210679 A1   7/2017   Chojecki et al.
(Continued)

FOREIGN PATENT DOCUMENTS

CN   101199940 A   6/2008
CN   1596150 A     3/2015
(Continued)

OTHER PUBLICATIONS

Feng Jiao, et al., "Selective conversion of syngas to light olefins", SCIENCE, Mar. 14, 2016 • vol. 351 Issue 6277, pp. 1065-1068.
(Continued)

*Primary Examiner* — Jafar F Parsa
(74) *Attorney, Agent, or Firm* — MagStone Law, LLP; Enshan Hong

(57) ABSTRACT

A supported catalyst for preparing light olefin using direct conversion of syngas is a composite catalyst and formed by compounding component I and component II in a mechanical mixing mode. The active ingredient of component I is a metal oxide; and the component II is a supported zeolite. A carrier is one or more than one of hierarchical pores $Al_2O_3$, $SiO_2$, $TiO_2$, $ZrO_2$, $CeO_2$, MgO and $Ga_2O_3$; the zeolite is one or more than one of CHA and AEI structures; and the load of the zeolite is 4%-45% wt. A weight ratio of the active ingredients in the component I to the component II is 0.1-20. The reaction process has an extremely high light olefin selectivity; the sum of the selectivity of the light olefin comprising ethylene, propylene and butylene can reach 50-90%, while the selectivity of a methane side product is less than 7%.

14 Claims, No Drawings

(51) Int. Cl.
*B01J 23/18* (2006.01)
*B01J 23/26* (2006.01)
*B01J 23/34* (2006.01)
*B01J 29/78* (2006.01)
*B01J 35/00* (2006.01)
*B01J 35/10* (2006.01)
*B01J 37/04* (2006.01)

(56) References Cited

U.S. PATENT DOCUMENTS

2018/0194700 A1 7/2018 Pan et al.
2019/0031575 A1 1/2019 Pan et al.

FOREIGN PATENT DOCUMENTS

| CN | 106311317 A | 1/2017 |
| CN | 106345514 A | 1/2017 |
| CN | 106660894 A | 5/2017 |
| CN | 107469857 A | 12/2017 |
| CN | 107774302 A | 3/2018 |
| EP | 2055380 A1 | 5/2009 |

OTHER PUBLICATIONS

International Search Report dated Apr. 23, 2019 for related International Patent Application No. PCT/CN2019/073386 issued by the international searching authority.

Written Opinion dated Apr. 18, 2019 for related International Patent Application No. PCT/CN2019/073386 issued by the international searching authority.

SUPPORTED CATALYST AND METHOD FOR PREPARING LIGHT OLEFIN USING DIRECT CONVERSION OF SYNGAS

RELATED APPLICATIONS

This is a U.S. national stage of international application No. PCT/CN2019/073386 filed on Jan. 28, 2019, which claims priority from China Patent Application No. 201810079249.4 filed on Jan. 26, 2018, the entire content of which is incorporated herein as reference.

TECHNICAL FIELD

The present invention belongs to preparation of light olefin using syngas, and particularly relates to a supported catalyst and a method for preparing light olefin using direct conversion of syngas.

BACKGROUND

Light olefin refers to alkene with the number of carbon atoms less than or equal to 4. Light olefin represented by ethylene and propylene are very important basic organic chemical raw materials. With the fast growth of economy in China, the market of the light olefin is in short supply for a long time. At present, the light olefin is produced mainly through a petrochemical route of cracking of light hydrocarbon (ethane, naphtha and light diesel fuel). Due to the increasing shortage of global petroleum resources and the long-term high-price operation of crude oil, the development of the light olefin industry relying only on a tubular cracking furnace technology that uses petroleum light hydrocarbon as raw material will encounter more and more difficulties in raw material. The production technology and the raw material of the light olefin must be diversified. A technology for preparing alkene using syngas can widen the source of the raw material, and will provide an alternative solution for a steam cracking technology based on high-cost raw material such as naphtha by production of syngas using crude oil, natural gas, coal and renewable material as raw material. One-step direct preparation of the light olefin using the syngas is a process of directly preparing the light olefin with the number of carbon atoms less than or equal to 4 through Fischer-Tropsch synthesis reaction of carbon monoxide and hydrogen under the action of the catalyst. This process simplifies the process flow and greatly reduces the investment unlike an indirect method that further prepares the alkene from the syngas and the methanol or dimethyl ether.

Direct preparation of the light olefin using the syngas through Fischer-Tropsch synthesis has become one of research hotspots in development of catalyst for Fischer-Tropsch synthesis. In patent CN1083415A disclosed by Dalian Institute of Chemical Physics, Chinese Academy of Sciences, high activity (CO conversion rate: 90%) and selectivity (light olefin selectivity: 66%) can be obtained under reaction pressure of 1.0 to 5.0 MPa and reaction temperature of 300 to 400° C. in preparation of the light olefin from the syngas under the auxiliary of alkali K or Cs ion by using an iron-manganese catalyst system carried by IIA alkali metal oxide such as MgO or silica rich zeolite (or phosphorous-aluminum zeolite). In patent ZL03109585.2 declared by Beijing University Of Chemical Technology, Fe/activated carbon catalyst with manganese, copper, zinc, silicon and potassium as auxiliaries is prepared by a vacuum impregnation method for the reaction of preparation of the light olefin from the syngas. Under the condition of no feedstock gas circulation, the CO conversion rate is 96%, and the selectivity of the light olefin in hydrocarbons is 68%. In 2012, professor de Jong's team at Utrecht university in Netherlands made good progress by using Fe catalyst modified by Fe, Na, S and other auxiliaries supported by SiC, carbon nanofiber and other inert carriers, obtained 61% of selectivity of light olefin. However, the selectivity is reduced when the conversion rate is increased. In 2016, researcher Sun Yuhan and researcher Zhong Liangshu in Shanghai Advanced Research Institute reported a preferred exposure [101] and [020] manganese-assisted cobalt carbide based catalyst, and realized 60.8% of selectivity of light olefin and 5% of selectivity of methane at a CO conversion rate of 31.8%. In the above report, the catalyst uses an iron or cobalt based catalyst as an active component. The reaction follows the chain growth reaction mechanism of metal surfaces. The selectivity of the product light olefin is low.

Recently, a composite bifunctional catalyst of $ZnCr_2O_4$ oxide and hierarchical pore SAPO-34 zeolite has been reported by academician Bao Xinhe and researcher Pan Xiulian in Dalian Institute of Chemical Physics, Chinese Academy of Sciences (Jiao et al., Science 351 (2016) 1065-1068), which has realized 80% of selectivity of the light olefin when the conversion rate of CO is 17%, wherein the selectivity of the light olefin is 14 and the alkene/alkane ratio is 5.7. When the conversion rate is increased to 35%, the alkene selectivity is 69%, alkane selectivity is 20%, and the alkene/alkane ratio is decreased to 3.5. How to achieve high conversion rate while stabilizing the alkene/alkane ratio is still a major difficulty in the field.

SUMMARY OF THE INVENTION

In view of the above problems, the present invention provides a catalyst and a method for preparing light olefin using direct conversion of syngas.

The technical solution of the present invention is: a catalyst comprises component I and component II; the component I and the component II are compounded in a mechanical mixing mode; an active ingredient of the component I is a metal oxide; the component II is a supported zeolite;

The metal oxide is one or more than one of $MnO_x$, $Mn_aCr_{(1-a)}O_x$, $Mn_aAl_{(1-a)}O_x$, $Mn_aZr_{(1-a)}O_x$, $Mn_aIn_{(1-a)}O_x$, $ZnO_x$, $Zn_aCr_{(1-a)}O_x$, $Zn_aAl_{(1-a)}O_x$, $Zn_aGa_{(1-a)}O_x$, $Zn_aIn_{(1-a)}O_x$, $CeO_x$, $Co_aAl_{(1-a)}O_x$, $Fe_aAl_{(1-a)}O_x$, $GaO_x$, $BiO_x$, $InO_x$, $In_aAl_bMn_{(1-a-b)}O_x$ and $In_aGa_bMn_{(1-a-b)}O_x$.

The specific surface area of $MnO_x$, $ZnO_x$, $CeO_x$, $GaO_x$, $BiO_x$ and $InO_x$ is 1-100 $m^2/g$; and a preferred specific surface area is 50-100 $m^2/g$.

The specific surface area of $Mn_aCr_{(1-a)}O_x$, $Mn_aAl_{(1-a)}O_x$, $Mn_aZr_{(1-a)}O_x$, $Mn_aIn_{(1-a)}O_x$, $Zn_aCr_{(1-a)}O_x$, $Zn_aAl_{(1-a)}O_x$, $Zn_aGa_{(1-a)}O_x$, $Zn_aIn_{(1-a)}O_x$, $Co_aAl_{(1-a)}O_x$, $Fe_aAl_{(1-a)}O_x$, $In_aAl_bMn_{(1-a-b)}O_x$ and $In_aGa_bMn_{(1-a-b)}O_x$ is 5-150 $m^2/g$; and a preferred specific surface area is 50-150 $m^2/g$.

The value range of x is 0.7-3.7, and the value range of a is 0-1; and the value range of a+b is 0-1.

a, b, (1-a), (1-a-b) and x in the present invention only represent the relative proportions of the chemical composition of the elements in the metal oxide. Any metal oxide with the same proportion is regarded as the same metal oxide.

A carrier of the supported zeolite is one or more than one of hierarchical pores $Al_2O_3$, $SiO_2$, $TiO_2$, $ZrO_2$, $CeO_2$, MgO and $Ga_2O_3$; the zeolite is one or more than one of CHA and AEI structures; and the load of the zeolite is 4%-45% wt.

The specific surface area of the carrier is 30-250 $m^2/g$.

Through calculation according to the specific surface area, mesoporous specific surface area occupies 30-75% and macroporous specific surface area occupies 25-70% in the carrier.

The zeolite is dispersed around the carrier by in situ growth or physical mixing mode.

A weight ratio of the active ingredients in the component I to the component II is 0.1-20, and preferably 0.3-5.

A dispersing agent is also added to the component I; the metal oxide is dispersed in the dispersing agent; and the dispersing agent is one or more than one of 3, $Al_2O_3$, $SiO_2$, $Cr_2O_3$, $ZrO_2$, $TiO_2$, $Ga_2O_3$, activated carbon, graphene and carbon nanotube. In the component I, the content of the dispersing agent is 0.05-90 wt %, and the balance is the metal oxide.

A method for preparing ethylene with high selectivity through syngas reaction uses syngas as reaction raw material; a conversion reaction is conducted on a fixed bed or a moving bed to obtain a light olefin product which mainly comprises ethylene; and an adopted catalyst is any of the above catalyst.

The pressure of the syngas is 0.5-10 MPa, preferably 1-8 MPa and more preferably 2-8 MPa; reaction temperature is 300-600° C., and preferably 300V-450V; space velocity is 300-10000 $h^{-1}$, preferably 500-900011$^{-1}$ and more preferably 500-6000 $h^{-1}$. The syngas is $H_2$/CO mixture; the molar ratio of $H_2$/CO is 0.2-3.5, and preferably 0.3-2.5. The syngas can also include $CO_2$, wherein the volume concentration of $CO_2$ in the syngas is 0.1-50%.

The catalyst is used for preparing light olefin using one-step direct conversion of syngas, wherein the sum of the selectivity of ethylene and propylene reaches 40-60%; the sum of the selectivity of the light olefin comprising ethylene, propylene and butylene can reach 50-90%, while the selectivity of a methane side product is less than 7%.

The present invention has the following advantages:

1. Different from the traditional technology for preparing the light olefin through methanol (MTO for short), this technology realizes preparation of the light olefin through one-step direct conversion of syngas.

2. On one hand, the role of the component II in the catalyst is to further convert the active gas-phase intermediate produced by the component I to obtain light olefin by coupling with the component I. The role of the component II on the balanced pull of the series reaction can promote the activation and conversion of the component I for the syngas and thus can increase the conversion rate. On the other hand, the special porous channel structure of the zeolite in the component II used in the present invention has a unique selection effect and can obtain more ethylene products with high selectivity.

3. The functions of the present invention cannot be achieved if the component I or the component II in the present invention is used separately. For example, the selectivity of methane in the product after separate use of the component I is very high, and the conversion rate is very low. The syngas cannot be activated and converted if the component II is used separately. Only the synergistic catalysis of the component I and the component II can achieve efficient conversion of the syngas and obtain excellent selectivity. Because the component I can activate the syngas to generate a specific active gas-phase intermediate, the intermediate diffuses into the porous channel of the component II through the gas phase. The zeolite of the CHA and AEI structures selected in the present invention has special pore structure and acidity which can effectively further activate and convert the active gas-phase intermediate produced by the component I into olefin. The special porous channel structure of the component II enables the product to have special selectivity.

4. The active ingredient metal oxide of the component I in the catalyst has a higher specific surface area; therefore, the metal oxide surface has more active sites, which is more conducive to conducting a catalytic reaction.

5. Because of the hierarchical pore carrier dispersed zeolite, it is beneficial to the mass transfer of the intermediate and the product, thereby greatly reducing the influence of side reactions such as hydrogenation (avoiding hydrogenation to produce alkane, such as ethane, propane and butane) and maintaining high selectivity of the light olefin while increasing the conversion rate.

6. The preparation process of the composite catalyst of the present invention is simple and has mild conditions. The reaction process has an extremely high product yield and selectivity, with the selectivity for $C_2$-$C_4$ light olefin reaching 50-90% and especially can still maintain high alkene/alkane ratio after increasing the conversion rate. Meanwhile, the selectivity of the methane side product is low (<7%), and the catalyst has long service life (>700 hours). The present invention has excellent application prospect.

DETAILED DESCRIPTION OF PREFERRED EMBODIMENTS

The present invention is further illustrated below by embodiments, but the scope of claims of the present invention is not limited by the embodiments. Meanwhile, the embodiments only give some conditions for achieving the purpose, but it doesn't mean that the conditions must be satisfied to achieve the purpose.

The metal oxide of the component I in the present invention can be obtained by purchasing a commercially available metal oxide with a high specific surface area, or obtained by the following embodiments:

The zeolite of component II of the present invention can be a zeolite prepared by the methods in the following embodiments, but is not limited to the following methods, and all zeolites that can satisfy the requirements of the present invention can be applied to the present invention.

Embodiment 1

I. Preparation of Component I of Catalyst (I) ZnO material with high specific surface area was synthesized through a precipitation method:

(1) 3 parts of 0.446 g (1.5 mmol) of $Zn(NO_3)_2.6H_2O$ were respectively weighed into three containers; 0.300 g (7.5 mmol), 0.480 g (12 mmol) and 0.720 g (18 mmol) of NaOH were respectively weighed and successively added to the above three containers; 30 ml of deionized water was weighed and added to the three containers; stirring was conducted for a time greater than 0.5 h at 70V to uniformly mix a solution; natural cooling was conducted to room temperature; reaction liquid was centrifugally separated to collect the centrifugally separated precipitate; and washing was conducted with deionized water twice to obtain ZnO metal oxide precursor;

(2) roasting: after drying the obtained product in the air, the product was roasted in an atmosphere to obtain ZnO material with high specific surface area. The atmosphere is inert gas, reducing gas or oxidizing gas. The inert gas is one or more than one of $N_2$, He and Ar. The reducing gas is one or two of $H_2$ and CO, and the reducing gas may also contain the inert gas. The oxidizing gas is one or more than one of $O_2$, $O_3$ and $NO_2$, and the oxidizing gas may also contain the inert gas. Roasting temperature is 300-700° C., and time is 0.5 h-12 h.

The purpose of roasting is to decompose the precipitated metal oxide precursor into oxide nanoparticles with high specific surface area at high temperature, and clean the adsorbed species on the surface of the oxide generated by decomposition through the high temperature roasting treatment.

Specific samples and preparation conditions thereof are shown in Table 1 below. As a reference example, ZnO #4 in the table is a commercially available ZnO single crystal with low specific surface area.

TABLE 1

Preparation of ZnO Material and Parameter Performance

| Zinc Oxide Sample Number | Roasting Time/h | Roasting Temperature/° C. | Roasting Atmosphere | Specific Surface Area $m^2/g$ |
|---|---|---|---|---|
| ZnO#1 | 5 | 500 | Ar | 71 |
| ZnO#2 | 2 | 320 | 5% $H_2/N_2$ | 47 |
| ZnO#3 | 3 | 550 | Air | 15 |
| ZnO#4 | — | — | — | <1 |

(II) MnO material with high specific surface area was synthesized through a coprecipitation method:

The preparation process is the same as that of the above ZnO #2. The difference is that, the precursor of Zn is changed for the corresponding precursor of Mn, which may be one of manganous nitrate, manganese chloride and manganese acetate, and is manganous nitrate herein. The corresponding product is defined as MnO. The specific surface area is 23 $m^2/g$.

(III) $CeO_2$ material with high specific surface area was synthesized through a coprecipitation method:

The preparation process is the same as that of the above ZnO #2. The difference is that, the precursor of Zn is changed for the corresponding precursor of Ce, which may be one of cerium nitrate, cerium chloride and cerous acetate, and is cerium nitrate herein. The corresponding product is defined as $CeO_2$. The specific surface area is 92 $m^2/g$.

(IV) $Ga_2O_3$ material with high specific surface area was synthesized through a coprecipitation method:

The preparation process is the same as that of the above ZnO #2. The difference is that, the precursor of Zn is changed for the corresponding precursor of Ga, which may be one of gallium nitrate, gallium chloride and gallium acetate, and is gallium nitrate herein. The corresponding product is defined as $Ga_2O_3$. The specific surface area is 55 $m^2/g$.

(V) $Bi_2O_3$ material with high specific surface area was synthesized through a coprecipitation method:

The preparation process is the same as that of the above ZnO #2. The difference is that, the precursor of Zn is changed for the corresponding precursor of Bi, which may be one of bismuth nitrate, bismuth chloride and bismuth acetate, and is bismuth nitrate herein. The corresponding product is defined as $Bi_2O_3$. The specific surface area is 87 $m^2/g$.

(VI) $In_2O_3$ material with high specific surface area was synthesized through a coprecipitation method:

The preparation process is the same as that of the above ZnO #2. The difference is that, the precursor of Zn is changed for the corresponding precursor of In, which may be one of indium nitrate, indium chloride and indium acetate, and is indium nitrate herein. The corresponding product is defined as $In_2O_3$. The specific surface area is 52 $m^2/g$.

(VII) $Mn_aCr_{(1-a)}O_x$, $Mn_aAl_{(1-a)}O_x$, $Mn_aZr_{(1-a)}O_x$, $Mn_aIn_{(1-a)}O_x$, $Zn_aCr_{(1-a)}O_x$, $Zn_aAl_{(1-a)}O_x$, $Zn_aGa_{(1-a)}O_x$, $Zn_aIn_{(1-a)}O_x$, $Co_aAl_{(1-a)}O_x$, $Fe_aAl_{(1-a)}O_x$, $In_aAl_bMn_{(1-a-b)}O_x$ and $In_aGa_bMn_{(1-a-b)}O_x$ with high specific surface area were synthesized through a precipitation method Zinc nitrate, aluminum nitrate, chromic nitrate, manganese nitrate, zirconium nitrate, indium nitrate, cobalt nitrate and ferric nitrate were adopted as precursors, and mixed at room temperature in water (wherein for ammonium carbonate as a precipitant, a feeding ratio is excessive or the ratio of ammonium ions to metal ions is preferably 1:1). The above mixed solution was aged, and then taken out for washing, filtering and drying; and the obtained solid was roasted under an air atmosphere to obtain a metal oxide with high specific surface area. Specific samples and preparation conditions thereof are shown in Table 2 below.

TABLE 2

Preparation of Metal Oxide with High Specific Surface Area and Performance Parameters

| Metal Oxide | Feeding Ratio of Metal Elements and Final Molar Concentration of One Metal in Water (mmol/L) | Aging Temperature ° C. | Aging Time h | Roasting Temperature ° C. | Roasting Time h | Specific Surface Area $m^2/g$ |
|---|---|---|---|---|---|---|
| $ZnCr_2O_4$ | ZnCr = 1:2, and Zn is 50 mM | 120 | 24 | 500 | 2 | 126 |
| $ZnAl_2O_4$ | ZnAl = 1:2, and Zn is 50 mM | 130 | 20 | 400 | 4 | 137 |
| $ZnGa_2O_4$ | ZnGa = 1:2, and Zn is 50 mM | 130 | 20 | 400 | 4 | 110 |
| $ZnIn_2O_4$ | ZnIn = 1:2, and Zn is 50 mM | 130 | 20 | 400 | 4 | 87 |
| $MnCr_2O_4$ | MnCr = 1:2, and Mn is 50 mM | 140 | 18 | 450 | 3 | 11 |
| $MnAl_2O_4$ | MnAl = 1:2, y = 2; and Mn is 50 mM | 145 | 16 | 400 | 2 | 15 |
| $MnZr2O_4$ | MnZr = 1:2, and Mn is 50 mM | 150 | 12 | 500 | 1 | 38 |

TABLE 2-continued

Preparation of Metal Oxide with High Specific Surface Area and Performance Parameters

| Metal Oxide | Feeding Ratio of Metal Elements and Final Molar Concentration of One Metal in Water (mmol/L) | Aging Temperature °C. | Aging Time h | Roasting Temperature °C. | Roasting Time h | Specific Surface Area m²/g |
|---|---|---|---|---|---|---|
| $MnIn_2O_4$ | MnIn = 1:2, and Mn is 50 mM | 150 | 12 | 500 | 1 | 67 |
| $COAl_2O_4$ | CoAl = 1:2, and Co is 50 mM | 145 | 16 | 400 | 2 | 22 |
| $FeAl_2O_4$ | FeAl = 1:2, and Fe is 50 mM | 145 | 16 | 400 | 2 | 30 |
| $InAl3MnO_7$ | In:Al:Mn = 1:3:1, and Mn is 50 mM | 150 | 12 | 500 | 1 | 84 |
| $InGa_2MnO_7$ | In:Ga:Mn = 1:2:1, and Mn is 50 mM | 145 | 16 | 400 | 2 | 67 |

(VIII) Metal oxide dispersed in dispersing agent $Cr_2O_3$, $Al_2O_3$ or $ZrO_2$ $Cr_2O_3$, $Al_2O_3$ or $ZrO_2$ dispersed metal oxide was prepared through a precipitate deposition method by taking $Cr_2O_3$, $Al_2O_3$ or $ZrO_2$ as a carrier. By taking preparation of dispersed ZnO as an example (the specific surface area is about 5 m²/g), commercial $Cr_2O_3$, $Al_2O_3$ (the specific surface area is about 20 m²/g) or $ZrO_2$ (the specific surface area is about 10 m²/g) as a carrier was dispersed in water in advance, and then mixed and precipitated at room temperature with a sodium hydroxide precipitant by taking zinc nitrate as raw material. The molar concentration of $Zn^{2+}$ is 0.067M; and the ratio of molar fractions of $Zn^{2+}$ and the precipitant is 1:8; and then aging was conducted at 160V for 24 hours to obtain dispersed ZnO by taking $Cr_2O_3$, $Al_2O_3$ or $ZrO_2$ as the carrier (the contents of the dispersing agents in the component I are 0.1 wt %, 20 wt % and 85 wt %). The obtained sample was roasted at 500V for 1 hour in air. The products are successively defined as dispersed oxides 1-3, and the specific surface areas are successively 148 m²/g, 115 m²/g and 127 m²/g.

The same method is used to obtain dispersed MnO oxide by taking $SiO_2$ (the specific surface area is about 2 m²/g), $Ga_2O_3$ (the specific surface area is about 10 m²/g), or $TiO_2$ (the specific surface area is about 15 m²/g) as the carrier (the contents of the dispersing agents in the component I are 5 wt %, 30 wt % and 60 wt %). The products are successively defined as dispersed oxides 4-6. The specific surface areas are successively 97 m²/g, 64 m²/g and 56 m²/g.

The same method is used to obtain dispersed ZnO oxide by taking activated carbon (the specific surface area is about 1000 m²/g), graphene (the specific surface area is about 500 m²/g), or carbon nanotube (the specific surface area is about 300 m²/g) as the carrier (the contents of the dispersing agents in the component I are 5 wt %, 30 wt % and 60 wt %). The products are successively defined as dispersed oxides 7-9. The specific surface areas are successively 177 m²/g, 245 m²/g and 307 m²/g.

II. Preparation of Component II (Zeolite of CHA and AEI Topology):

The CHA and/or AEI topology has eight-membered ring orifices and a three-dimensional porous channel and comprises cha cage.

1) The specific preparation process is as follows, but is not limited to the following method:

The raw materials of 30% (mass concentration) of silica sol, AlOOH, phosphoric acid, TEA (R) and deionized water were weighed according to oxide $SiO_2$:$Al_2O_3$:$H_3PO_4$:R:$H_2O$=1.6:16:32:55:150 (mass ratio); after mixing at room temperature, 0.5 time of molar weight of auxiliary HF was added to a template agent; carrier oxide powder was added; the mixture was stirred and aged at 30V and then transferred into a hydrothermal reactor after 2 h, and crystallized at 200 V for 24 h. The water bath was quenched to room temperature. Centrifugal washing was conducted repeatedly so that the pH of the supernatant is 7 at the end of washing. After the precipitate was dried at 110 V for 17 h, the precipitate was calcined in air at 600 V for 3 h to obtain the supported silicon-phosphorus-aluminum inorganic solid acid.

The skeleton element composition of the zeolite of CHA and AEI topologies may be one or more than two of Si—O, Si—Al—O, Si—Al—P—O, Al—P—O, Ga—P—O, Ga—Si—Al—O, Zn—Al—P—O, Mg—Al—P—O and Co—Al—P—O.

O element of part of the skeleton is connected with H, and corresponding products are successively defined as parts 1-8.

TABLE 3

Preparation of Zeolite of CHA or AEI Topology and Performance Parameters

| Sample Number | Si Source | Aluminum Source | P Source | Template Agent | Auxiliary | Mass Ratio |
|---|---|---|---|---|---|---|
| part 1 | TEOS | sodium metaaluminate | phosphoric acid | TEA |  | $SiO_2$:$Al2O_3$:$H_3PO_4$:R:$H_2O$ = 1.6:16:32:55:150 |
| part 2 | silica sol | Al(OH)3 | phosphoric acid | Mor | HCl | $SiO_2$:$Al_2O_3$:$H_3PO_4$:R:$H_2O$ = 2.4:19:30:15:150 |
| part 3 | TEOS | AlOOH | phosphoric acid | TEAOH | HF | $SiO_2$:$Al_2O_3$:$H_3PO_4$:R:$H_2O$ = 0.7:15:32:55:150 |
| part 4 | silica sol | aluminum isopropoxide | phosphoric acid | DIPEA |  | $SiO_2$:$Al_2O_3$:$H_3PO_4$:R:$H_2O$ = 1.1:17:32:55:150 |

TABLE 3-continued

Preparation of Zeolite of CHA or AEI Topology and Performance Parameters

| | Precursor 1 | Precursor 2 | Precursor 3 | Template Agent | Auxiliary | Mass Ratio |
|---|---|---|---|---|---|---|
| part 5 | | aluminum sulfate | phosphoric acid | TEAOH | HF | $Al_2O_3:H_3PO_4:R:H_2O = 16:32:55:150$ |
| part 6 | silica sol | aluminum nitrate | phosphoric acid | DIPEA | | $SiO_2:Al_2O_3:H_3PO_4:R:H_2O = 0.5:17:32:55:150$ |
| part 7 | TEOS | aluminum sulfate | phosphoric acid | TEA | HF | $SiO_2:Al_2O3:H_3PO_4:R:H_2O = 0.3:18:32:55:150$ |
| part 8 | | acid aluminum | acid | EA | HCl | $Al_2O_3:H_3PO_4:R:H_2O = 11:32:55:150$ |

2) Zeolite composed of other elements

| Sample Number | Precursor 1 | Precursor 2 | Precursor 3 | Template Agent | Auxiliary | Mass Ratio |
|---|---|---|---|---|---|---|
| part 9 | TEOS | | | TEA | HF | $SiO_2:R:H_2O = 1.6:55:150$ |
| part 10 | silica sol | Al(OH)3 | | Mor | HF | $SiO_2:Al_2O_3:R:H_2O = 2.4:19:15:150$ |
| part 11 | | gallium nitrate | phosphoric acid | TEAOH | HF | $Ga_2O_3:H^3PO_4:R:H_2O = 15:32:55:150$ |
| part 12 | silica sol | gallium nitrate | phosphoric acid | TEA | HF | $SiO_2:Ga_2O_3:H_3PO_4:R:H_2O = 1.1:17:32:55:150$ |
| part 13 | zinc nitrate | aluminum sulfate | phosphoric acid | TEAOH | HF | $ZnO:Al_2O_3:H_3PO_4:R:H_2O = 0.5:16:32:55:150$ |
| part 14 | magnesium nitrate | aluminum nitrate | phosphoric acid | TEA | | $MgO:Al_2O_3:H_3PO_4:R:H_2O = 0.5:17:32:55:150$ |
| part 15 | gallium nitrate | aluminum sulfate | phosphoric acid | TEA | HF | $Ga_2O_3:Al_2O_3:H_3PO_4:R:H_2O = 0.4:18:32:55:150$ |

| Sample Number | Hydrothermal Temperature/° C. | Time (Day) | Carrier | Zeolite Load wt % |
|---|---|---|---|---|
| part 1 | 180 | 1 | Al2O3 | 4 |
| part 2 | 150 | 4 | SiO2 | 15 |
| part 3 | 160 | 4 | TiO2 | 28 |
| part 4 | 170 | 2.5 | ZrO2 | 34 |
| part 5 | 190 | 1 | CeO2 | 24 |
| part 6 | 200 | 1 | MgO | 8 |
| part 7 | 170 | 0.7 | Ga2O3 | 20 |
| part 8 | 160 | 3.5 | Al2O3 | 31 |

2) Zeolite composed of other elements

| Sample Number | Hydrothermal Temperature (° C.) | Time (Day) | Carrier | Zeolite Load wt % |
|---|---|---|---|---|
| part 9 | 180 | 1 | SiO2 | 45 |
| part 10 | 150 | 4 | Al2O3 | 10 |
| part 11 | 160 | 4 | TiO2 | 22 |
| part 12 | 170 | 2.5 | ZrO2 | 6 |
| part 13 | 190 | 1 | CeO2 | 25 |
| part 14 | 200 | 1 | MgO | 8 |
| part 15 | 170 | 0.7 | Ga2O3 | 11 |

The reference example is part 16; other conditions are the same as those of part 1; and the zeolite load is changed to 1%.

The reference example is part 17; other conditions are the same as those of part 1; and the zeolite load is changed to 70%.

III. Catalyst Preparation

The component I and the component II in the required ratio were added to the container to achieve the purposes of separation, crushing, uniform mixing and the like through one or more than two of extrusion force, impact force, shear force and friction force generated by high-speed motion of the material and/or the container, so as to realize conversion of mechanical energy, thermal energy and chemical energy by regulating the temperature and the atmosphere of carrier gas, thereby further enhancing the interaction between different components.

In the mechanical mixing process, the mixing temperature can be set as 20-100° C., and the mechanical mixing process can be conducted in an atmosphere or directly in the air. The atmosphere is selected from any of the following gas:

a) nitrogen and/or inert gas;

b) mixed gas of hydrogen, nitrogen and/or inert gas, with the volume of hydrogen in the mixed gas being 5-50%;

c) mixed gas of CO, nitrogen and/or inert gas, with the volume of CO in the mixed gas being 5-20%;

d) mixed gas of $O_2$, nitrogen and/or inert gas, with the volume of $O_2$ in the mixed gas being 5-20%, wherein the inert gas is one or more than one of helium, argon and neon.

The mechanical mixing can adopt one or more than one of mechanical agitation, ball milling, rocking bed mixing and mechanical grinding for composition. Specifically:

Mechanical stirring: mixing the component I and the component II with a stirring rod in a stirring tank; and regulating the mixing degree of the component I and the component II by controlling stirring time (5 min-120 min) and rate (30-300 r/min).

Ball milling: rolling at high speed in a grinding tank by using abrasive and the catalysts; and producing strong impact and milling on the catalysts to achieve the effects of dispersing and mixing the component I and the component II. The ratio of the abrasive (which is stainless steel, agate and quartz; and the size range is 5 mm-15 mm) to the catalysts (the mass ratio range is 20-100:1) is controlled.

Shaking table mixing: premixing the component I and the component II and placing the components into the container; realizing the mixing of the component I and the component II by controlling the reciprocating oscillation or circumferential oscillation of a shaking table; and realizing uniform mixing by regulating oscillation speed (range: 1-70 r/min) and time (range: 5 min-120 min).

Mechanical grinding: premixing the component I and the component II and placing the components into the container; and under certain pressure (range: 5 kg-20 kg), making relative motion (speed range: 30-300 r/min) by an abrader and mixed catalysts to achieve the effect of uniform mixing.

Specific catalyst preparation and parameter features are shown in Table 4.

TABLE 4

Preparation of Catalysts and Parameter Features

| | | | | Compounding Mode and Condition | | | |
|---|---|---|---|---|---|---|---|
| Catalyst Number | Catalyst Component I | Catalyst Component II | Weight Ratio of I to II | Mechanical Agitation Rate (r/min) and Time (min) | Ball Milling Abrasive Material, Size Range and Catalyst Mass Ratio | Rocking Bed Oscillation Speed (r/min) and Time (min) | Mechanical Polishing Pressure (kg) and Relative Movement Rate (r/min) |
| A | ZnO#1 | part 1 | 0.33 | 170, 60 | | | |
| B | ZnO#2 | part 2 | 0.5 | 10, 50 | | | |
| C | ZnO#3 | part 3 | 2 | | 5 mm stainless steel ball 30:1 | | |
| D | MnO | part 4 | 1 | | 6 mm stainless steel ball, 600:1 | | |
| E | $CeO_2$ | part 5 | 1 | | | 5, 10 | |
| F | $Bi_2O_3$ | part 6 | 3 | | | 60, 100 | |
| G | $In_2O_3$ | part 7 | 3 | | | | 50, 30 |
| H | $Ga_2O_3$ | part 8 | 1 | 100, 300 | | | |
| I | $ZnCr_2O_4$ | part 9 | 5 | | 6 mm agate ball, 110:1 | | |
| J | $ZnAl_2O_4$ | part 10 | 1 | | | 70, 100 | |
| K | $ZnGa_2O_4$ | part 11 | 3 | | | | 5, 20 |
| L | $ZnIn_2O_4$ | part 12 | 0.33 | | | | 2, 30 |
| M | $MnCr_2O_4$ | part 13 | 1 | 10, 10 | | | |
| N | $MnAl_2O_4$ | part 14 | 3 | | 6 mm quartz, 10:1 | | |
| O | $MnZr_2O_4$ | part 15 | 0.33 | | 6 mm quartz, 10:1 | | |
| P | $MnIn_2O_4$ | part 1 | 1 | | | | 1, 10 |
| Q | $CoAl_2O_4$ | part 2 | 1 | 200, 250 | | | |
| R | $FeAl_2O_4$ | part 3 | 3 | | 5 mm stainless steel ball, 50:1 | | |
| S | $InAl_3MnO_7$ | part 4 | 1 | | | | 10, 100 |
| T | $InGa_2MnO_7$ | part 5 | 4 | | | 50, 600 | |
| U | dispersed oxide 1 | part 6 | 3 | | | | 10, 100 |
| V | dispersed oxide 2 | part 7 | 20 | | 5 mm stainless steel ball, 10:1 | | |
| W | dispersed oxide 3 | part 8 | 0.5 | 5, 30 | | | |
| X | dispersed oxide 4 | part 9 | 1 | 100, 250 | | | |
| Y | dispersed oxide 5 | part 10 | 3 | | 5 mm stainless steel ball, 200:1 | | |
| Z | dispersed oxide 6 | part 11 | 1.5 | | 6 mm stainless steel ball, 60:1 | | |

TABLE 4-continued

Preparation of Catalysts and Parameter Features

| | | | | Compounding Mode and Condition | | | |
|---|---|---|---|---|---|---|---|
| Catalyst Number | Catalyst Component I | Catalyst Component II | Weight Ratio of I to II | Mechanical Agitation Rate (r/min) and Time (min) | Ball Milling Abrasive Material, Size Range and Catalyst Mass Ratio | Rocking Bed Oscillation Speed (r/min) and Time (min) | Mechanical Polishing Pressure (kg) and Relative Movement Rate (r/min) |
| Z1 | dispersed oxide 7 | part 12 | 2.5 | | | 70, 100 | |
| Z2 | dispersed oxide 8 | part 13 | 1.5 | | | 60, 100 | |
| Z3 | dispersed oxide 9 | part 14 | 2 | | | | 50, 30 |
| Reference example 1 | ZnO#4 | part 1 | 3 | | | 20, 30 | |
| Reference example 2 | composite metal ZnCo, the molar ratio of Zn to Co is 1:1. | part 3 | 2 | | 5 mm stainless steel ball, 30:1 | | |
| Reference example 3 | $TiO_2$ | part 3 | 2 | | 5 mm stainless steel ball, 30:1 | | |

Example of Catalytic Reactions

A fixed bed reaction was taken as an example, but the catalyst was also applicable to a fluidized bed reactor. The apparatus was equipped with gas mass flow meters and online product analysis chromatography (the tail gas of the reactor is directly connected with the metering valve of chromatography, and thus periodic and real-time sampling and analysis will be achieved).

2 g of the above catalyst in the present invention was placed in a fixed bed reactor. The air in the reactor was replaced with Ar; and then the temperature was raised to 300° C. in the $H_2$ atmosphere, and then the syngas ($H_2$/CO molar ratio=0.2-3.5) wa switched. The pressure of the syngas was 0.5-10 MPa. The temperature was raised to reaction temperature of 300-600° C., and the air velocity of the reaction raw gas was regulated to 500-10000 ml/g/h. On-line chromatography was used to detect and analyze the product.

The reaction performance can be changed by changing the temperature, pressure, space velocity and $H_2$/CO molar ratio in the syngas. The sum of selectivity of the light olefin, the ethylene, the propylene and the butylene is 50-90%. Due to the low hydrogenation activity of the surface of the metal composite of the catalyst, a large amount of methane will not be avoided and the selectivity of the methane is low. Table 5 lists specific application and effect data of the catalysts.

TABLE 5

Specific Application and Effect Data of Catalysts

| Embodiment | Catalyst | GHSV ($h^{-1}$) | Temperature (° C.) | H2/CO Molar Ratio | Pressure (MPa) | CO Conversion Rate % | Light Olefin Selectivity % | $CH_4$ Selectivity % | Alkene/alkane ratio |
|---|---|---|---|---|---|---|---|---|---|
| 1 | A | 8000 | 410 | 2 | 3.5 | 23.7 | 86.4 | 5.1 | 15.7 |
| 2 | B | 3000 | 400 | 5.5 | 0.9 | 38.3 | 84.6 | 5.2 | 11.3 |
| 3 | C | 8000 | 380 | 3 | 4.5 | 24.4 | 84.5 | 2.6 | 11.9 |
| 4 | D | 3000 | 370 | 6 | 10 | 32.6 | 71.0 | 6.5 | 5.0 |
| 5 | E | 10000 | 470 | 3.5 | 1.5 | 27.8 | 77.3 | 4.3 | 6.7 |
| 6 | F | 2000 | 400 | 4.5 | 7 | 55.5 | 83.2 | 2.9 | 9.0 |
| 7 | G | 3000 | 380 | 6.5 | 2.5 | 37.2 | 75.7 | 6.7 | 9.3 |
| 8 | H | 500 | 370 | 8.5 | 5 | 30.7 | 68.9 | 6.8 | 6.1 |
| 9 | I | 2300 | 370 | 1 | 3.5 | 28.1 | 73.7 | 5.1 | 10.2 |
| 10 | J | 4000 | 410 | 2.5 | 5 | 37.0 | 87.7 | 2.1 | 16.3 |
| 11 | K | 1000 | 430 | 2.5 | 3 | 58.1 | 82.2 | 4.9 | 13.7 |
| 12 | L | 9500 | 520 | 1 | 4 | 19.3 | 86.9 | 6.1 | 15.8 |
| 13 | M | 600 | 480 | 0.5 | 9 | 14.0 | 67.7 | 6.5 | 5.6 |
| 14 | N | 9100 | 470 | 3 | 6 | 37.8 | 86.3 | 2.5 | 13.6 |
| 15 | O | 8200 | 450 | 1.5 | 5 | 36.6 | 85.5 | 2.4 | 13.9 |
| 16 | P | 8000 | 450 | 2.5 | 5 | 33.6 | 87.8 | 2.7 | 15.6 |
| 17 | Q | 600 | 350 | 3.5 | 5 | 27.4 | 75.5 | 3.4 | 7.6 |
| 18 | R | 2100 | 350 | 6 | 7 | 19.8 | 84.6 | 5.3 | 12.4 |
| 19 | S | 2500 | 400 | 4 | 6 | 57.5 | 79.6 | 5.1 | 13.5 |
| 20 | T | 4000 | 400 | 4 | 4 | 33.3 | 73.1 | 6.5 | 10.8 |
| 21 | U | 3500 | 400 | 4 | 3 | 27.9 | 75.1 | 6.7 | 7.0 |
| 22 | V | 8600 | 450 | 2.5 | 4 | 29.2 | 81.0 | 2.9 | 13.1 |
| 23 | W | 5500 | 410 | 0.3 | 3.5 | 19.8 | 82.6 | 3.7 | 15.4 |

TABLE 5-continued

Specific Application and Effect Data of Catalysts

| Embodiment | Catalyst | GHSV (h$^{-1}$) | Temperature (° C.) | H2/CO Molar Ratio | Pressure (MPa) | CO Conversion Rate % | Light Olefin Selectivity % | CH$_4$ Selectivity % | Alkene/alkane ratio |
|---|---|---|---|---|---|---|---|---|---|
| 24 | X | 3000 | 400 | 5.5 | 0.9 | 18.7 | 77.4 | 5.2 | 8.6 |
| 25 | Y | 2000 | 360 | 7 | 2.5 | 39.6 | 68.7 | 6.5 | 6.0 |
| 26 | Z | 800 | 370 | 5 | 10 | 41.3 | 73.8 | 6.6 | 5.9 |
| 27 | Z1 | 10000 | 470 | 1.5 | 1.5 | 17.5 | 76.0 | 6.3 | 15.8 |
| 28 | Z2 | 4000 | 400 | 3.5 | 7 | 49.8 | 84.5 | 3.7 | 17.7 |
| 29 | Z3 | 3000 | 380 | 5.5 | 2.5 | 25.4 | 72.5 | 6.7 | 6.9 |
| 38 | C | 4000 | 380 | 3 | 4.5 | 57.3 | 83.3 | 3.7 | 10.1 |
| 39 | J | 2000 | 410 | 2.5 | 5 | 55.7 | 85.3 | 2.4 | 10.2 |
| 40 | Reference example 1 | 3000 | 320 | 0.5 | 1 | 1.8 | 30.5 | 35.3 | 2.5 |
| 42 | Reference example 2 | 4000 | 450 | 3 | 3 | 3.5 | 31.3 | 29.2 | 1.8 |
| 43 | Reference example 2 | 2000 | 350 | 2.5 | 3 | 0.2 | 27.3 | 65.8 | 1.7 |
| 44 | Reference example 4 | 2000 | 410 | 1.5 | 3 | 26.7 | 46.2 | 11.7 | 1.5 |
| 45 | Reference example 5 | 3000 | 400 | 2 | 3.5 | 32.6 | 21.6 | 13.8 | 0.8 |
| 48 | Reference example 6 | 8000 | 380 | 3 | 4.5 | 7.8 | 65.5 | 18.0 | 4.3 |
| 49 | Reference example 6 | 4000 | 380 | 3 | 4.5 | 12.4 | 47.2 | 17.5 | 1.7 |
| 50 | Reference example 7 | 8000 | 380 | 3 | 4.5 | 37.3 | 49.9 | 2.5 | 1.5 |
| 51 | Reference example 7 | 4000 | 380 | 3 | 4.5 | 55.7 | 38.1 | 4.5 | 0.7 |
| 52 | Reference example 8 | 3000 | 450 | 2.5 | 4 | <0.01 | 1.5 | 50 | 0.8 |
| 53 | Reference example 9 | 2200 | 450 | 3 | 2 | <0.01 | — | — | — |

The catalyst component I in reference example 1 is ZnO #4. Other parameters and the mixing process are the same as those of catalyst C.

The component I in the catalyst adopted in reference example 2 is metal ZnCo. The molar ratio of ZnCo is 1:1. Other parameters and the mixing process are the same as those of catalyst C.

The component I in the catalyst adopted in reference example 3 is TiO$_2$. Other parameters and the mixing process are the same as those of catalyst C.

The zeolite of the component II in the catalyst adopted in reference example 4 is a commodity SAPO-34 purchased from Nankai University Catalyst Factory without carrier dispersion. Other parameters and the mixing process are the same as those of catalyst A.

The zeolite of the component II in the catalyst adopted in reference example 5 is a commodity ZSM-5 purchased from Nankai University Catalyst Factory, wherein the zeolite is of a full microporous structure, and the silica alumina ratio is 30, without carrier dispersion. Other parameters and the mixing process are the same as those of catalyst A.

Reaction results of reference examples 4 and 5 show that, the topology and the carrier dispersion of CHA or AEI are crucial to the selective modulation of the products.

For the catalysts in the reference examples 6 and 7, other conditions are the same as those of C; and only the zeolites are respectively replaced with part 16 and part 17.

It can be seen from the reference example 6 that, the zeolite load is too low, which results in slightly high selectivity of methane and slightly low selectivity of alkene.

It can be seen from the reference example 7 that, the zeolite load is too high, which results in excessive hydrogenation and slightly low selectivity of alkene. Especially after the space velocity is reduced and the conversion rate is increased, compared with the catalyst C, the alkene/alkane ratio is obviously reduced.

The catalyst adopted in reference example 8 is a sample containing only component IZnO #1 without the zeolite, and the reaction conversion rate is very low. The products mainly comprise by-products such as dimethyl ether and methane, and almost no ethylene is produced.

The catalyst adopted in reference example 9 is a sample containing only component II and MOR1 zeolite without the component I, and the catalytic reaction almost has no activity.

Reference examples 8 and 9 indicate that reaction effects are extremely poor when only component I or component II exists, and do not have the excellent reaction performance in the present invention. It is observed from the above table that, the structure of the zeolite including the topologies of CHA&AEI, and the matching between the zeolite and the metal oxide are crucial; and the responsibility of the zeolite further affects the conversion rate of carbon monoxide and propylene and butylene selectivity.

It is found from the life investigation conducted in embodiments 2, 6 and 16 that, three samples can keep the conversion rate and the selectivity unchanged in the stability experiment of 700 h. Compared with the literature (Jiao et al., Science 351(2016)1065-1068), although the conversion rate of the catalyst used in the literature maintains a stable conversion rate in the stability investigation of 650 h, the selectivity of the light olefin is obviously changed and the selectivity of the methane is increased. It indicates that the catalyst of the present invention has obvious advantages in stability.

The invention claimed is:

1. A catalyst, comprising component I and component II, which are compounded in a mechanical mixing mode; wherein, an active ingredient of the component I is a metal oxide; the component II is a supported zeolite;

the metal oxide is at least one of $MnO_x$, $Mn_aCr_{(1-a)}O_x$, $Mn_aAl_{(1-a)}O_x$, $Mn_aZr_{(1-a)}O_x$, $Mn_aIn_{(1-a)}O_x$, $ZnO_x$, $Zn_aCr_{(1-a)}O_x$, $Zn_aAl_{(1-a)}O_x$, $Zn_aGa_{(1-a)}O_x$, $Zn_aIn_{(1-a)}O_x$, $CeO_x$, $Co_aAl_{(1-a)}O_x$, $Fe_aAl_{(1-a)}O_x$, $GaO_x$, $BiO_x$, $InO_x$, $In_aAl_bMn_{(1-a-b)}O_x$ and $In_aGa_bMn_{(1-a-b)}O_x$;

a specific surface area of $MnO_x$, $ZnO_x$, $CeO_x$, $GaO_x$, $BiO_x$ and $InO_x$ is 1-100 m$^2$/g;

a specific surface area of $Mn_aCr_{(1-a)}O_x$, $Mn_aAl_{(1-a)}O_x$, $Mn_aZr_{(1-a)}O_x$, $Mn_aIn_{(1-a)}O_x$, $Zn_aCr_{(1-a)}O_x$, $Zn_aAl_{(1-a)}O_x$, $Zn_aGa_{(1-a)}O_x$, $Zn_aIn_{(1-a)}O_x$, $Co_aAl_{(1-a)}O_x$ $Fe_aAl_{(1-a)}O_x$, $In_aAl_bMn_{(1-a-b)}O_x$ and $In_aGa_bMn_{(1-a-b)}O_x$ is 5-150 m$^2$/g;

a value range of x is 0.7-3.7, and a value range of a is 0-1; and a value range of a+b is 0-1;

a carrier of the supported zeolite is at least one of hierarchical pores $Al_2O_3$, $SiO_2$, $TiO_2$, $ZrO_2$, $CeO_2$, MgO, and $Ga_2O_3$; the zeolite is one or two of CHA and AEI structures; and a load of the zeolite is 4%-45% wt, and through calculation according to the specific surface area, mesoporous specific surface area occupies 30-75%, and macroporous specific surface area occupies 25-70% in the carrier.

2. The catalyst according to claim 1, wherein a specific surface area of the carrier is 30-250 m$^2$/g.

3. The catalyst according to claim 1, wherein the zeolite is dispersed around the carrier by in situ growth or physical mixing mode.

4. The catalyst according to claim 1, wherein a weight ratio of the active ingredients in the component I to the component II is 0.1-20.

5. The catalyst according to claim 1, wherein a dispersing agent is also added to the component I; the metal oxide is dispersed in the dispersing agent; the dispersing agent is at least one of $Al_2O_3$, $SiO_2$, $Cr_2O_3$, $ZrO_2$, $TiO_2$, $Ga_2O_3$, activated carbon, graphene, and carbon nanotube.

6. The catalyst according to claim 1, wherein in the component I, a content of the dispersing agent is 0.05-90 wt %, and the balance is the metal oxide.

7. A method for preparing a light olefin product through syngas reaction comprising converting the syngas to the light olefin product in the presence of the catalyst of claim 1, wherein the light olefin product comprises ethylene.

8. The method according to claim 7, wherein the converting is conducted under a pressure of 0.5-10 MPa, a reaction temperature of 300-600° C., a space velocity of 300-10000 h$^{-1}$, the syngas is a $H_2$/CO mixture with a molar ratio of $H_2$/CO of 0.2-3.5.

9. The method according to claim 7, wherein the light olefin product comprises $C_{2-4}$ olefin, and the method achieves a selectivity of 50-90% for the $C_{2-4}$ olefin, and a selectivity of lower than 7% for a methane side product.

10. The catalyst according to claim 1, wherein the specific surface area of $MnO_x$, $ZnO_x$, $CeO_x$, $GaO_x$, $BiO_x$ and $InO_x$ is 50-100 m$^2$/g and the specific surface area of $Mn_aCr_{(1-a)}O_x$, $Mn_aAl_{(1-a)}O_x$, $Mn_aZr_{(1-a)}O_x$, $Mn_aIn_{(1-a)}O_x$, $Zn_aCr_{(1-a)}O_x$, $Zn_aAl_{(1-a)}O_x$, $Zn_aGa_{(1-a)}O_x$, $Zn_aIn_{(1-a)}O_x$, $Co_aAl_{(1-a)}O_x$ $Fe_aAl_{(1-a)}O_x$, $In_aAl_bMn_{(1-a-b)}O_x$ and $In_aGa_bMn_{(1-a-b)}O_x$ is 5-150 m$^2$/g.

11. The catalyst according to claim 1, wherein a weight ratio of the active ingredients in the component I to the component II is 0.3-5.

12. The method according to claim 7, wherein the converting is conducted under a pressure of 1-8 MPa, a reaction temperature of 300° C.-450° C., a space velocity of 500-9000 h$^{-1}$, the syngas is a $H_2$/CO mixture with a molar ratio of $H_2$/CO of 0.3-2.5, and the syngas also comprises $CO_2$, and a volume concentration of $CO_2$ in the syngas is 0.1-50%.

13. The method according to claim 12 wherein the pressure is 2-8 MPa, and the space velocity is 500-6000 h$^{-1}$.

14. The catalyst according to claim 1 wherein the metal oxide consist of at least one of $MnO_x$, $Mn_aCr_{(1-a)}O_x$, $Mn_aAl_{(1-a)}O_x$, $Mn_aZr_{(1-a)}O_x$, $Mn_aIn_{(1-a)}O_x$, $ZnO_x$, $Zn_aCr_{(1-a)}O_x$, $Zn_aAl_{(1-a)}O_x$, $Zn_aGa_{(1-a)}O_x$, $Zn_aIn_{(1-a)}O_x$, $CeO_x$, $Co_aAl_{(1-a)}O_x$, $Fe_aAl_{(1-a)}O_x$, $GaO_x$, $BiO_x$, $InO_x$, $In_aAl_bMn_{(1-a-b)}O_x$ and $In_aGa_bMn_{(1-a-b)}O_x$, and $In_aGa_bMn_{(1-a-b)}$.

* * * * *